(12) United States Patent
Aigle et al.

(10) Patent No.: US 9,439,873 B2
(45) Date of Patent: Sep. 13, 2016

(54) APPLICATION AID

(75) Inventors: Manuela Aigle, Sauerlach (DE); Björn Schurad, München (DE); Holger Piotrowski, Schliersee (DE)

(73) Assignee: ACINO AG (DE)

( * ) Notice: Subject to any disclaimer, the term of this patent is extended or adjusted under 35 U.S.C. 154(b) by 0 days.

(21) Appl. No.: 14/236,415

(22) PCT Filed: Aug. 3, 2012

(86) PCT No.: PCT/EP2012/065264
§ 371 (c)(1),
(2), (4) Date: Jan. 31, 2014

(87) PCT Pub. No.: WO2013/017689
PCT Pub. Date: Feb. 7, 2013

(65) Prior Publication Data
US 2014/0155845 A1    Jun. 5, 2014

(30) Foreign Application Priority Data
Aug. 3, 2011 (DE) .................. 10 2011 080 390

(51) Int. Cl.
| | | |
|---|---|---|
| *A61F 13/02* | (2006.01) | |
| *A61F 13/00* | (2006.01) | |
| *A61L 15/16* | (2006.01) | |
| *A61K 9/70* | (2006.01) | |
| *A61F 15/00* | (2006.01) | |
| *A61M 35/00* | (2006.01) | |

(52) U.S. Cl.
CPC ............. *A61K 9/7084* (2013.01); *A61K 9/703* (2013.01); *A61M 35/00* (2013.01)

(58) Field of Classification Search
None
See application file for complete search history.

(56) References Cited

U.S. PATENT DOCUMENTS

| | | | | |
|---|---|---|---|---|
| 5,958,447 | A | * | 9/1999 | Haralambopoulos .. A61K 9/703 424/401 |
| 6,129,929 | A | | 10/2000 | Wick |
| 2004/0234583 | A1 | * | 11/2004 | Muller ................. A61K 9/7092 424/449 |
| 2005/0037059 | A1 | * | 2/2005 | Miller ........................... 424/448 |
| 2007/0282238 | A1 | * | 12/2007 | Madsen ................ A61F 13/023 602/48 |
| 2008/0031933 | A1 | * | 2/2008 | Gale ..................... A61K 9/7023 424/449 |
| 2010/0178322 | A1 | | 7/2010 | Ameyama et al. |

FOREIGN PATENT DOCUMENTS

| | | |
|---|---|---|
| CA | 2 373 276 A1 | 12/2000 |
| EP | 0354315 A1 | 2/1990 |
| EP | 1967171 A1 | 9/2008 |
| EP | 2340815 A1 | 7/2011 |
| JP | 2008156323 A | 7/2008 |
| JP | 2010163367 A | 7/2010 |

OTHER PUBLICATIONS

Kim et al.; International Journal of Computer Science and Network Security (IJCSNS); vol. 10, No. 2, Feb. 2010.*
Inman, D. J.; Vibration with Control (2006); Appendix A; Comments on Units; pp. 357-359.*
Gregory, B. H.; Polyethylene Extrusion Coating and Film Lamination: The Complete Process Manual; excerpt; section 11.1; p. 250 (2012).*
Watson Pharma, Inc., OXYTROL® oxybutynin patch; published Jan. 2011 (pdf attached).*
International Search Report dated Oct. 24, 2012, for International Application No. PCT/EP2012/065264, in English and German (6 pages).

* cited by examiner

*Primary Examiner* — Jeffrey T Palenik
(74) *Attorney, Agent, or Firm* — Kilyk & Bowersox, P.L.L.C.

(57) ABSTRACT

The invention relates to a transdermal therapeutic system (10) comprising an active ingredient depot (11) that contains at least one active ingredient, comprising an application face which is designed for applying on a skin and which is adhesive on at least some parts of the surface, and comprising a protective film (14) which covers the application face and which comprises a first protective film part (14a) and a second protective film part (14b). The first protective film part (14a) differs from the second protective film part (14b) in terms of physical properties.

22 Claims, 3 Drawing Sheets

APPLICATION AID

Figure 1:
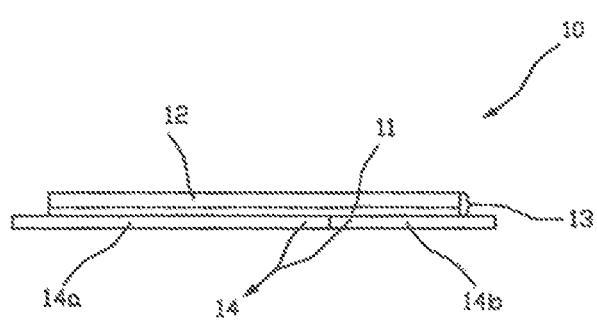

The present invention relates to application aids for transdermal therapeutic systems and in particular to protective coverings for transdermal therapeutic systems, which facilitate the application of the systems to the skin of a patient.

Transdermal therapeutic systems are applied generally to the skin of a patient in order to administer an active ingredient contained in the transdermal therapeutic system. Administration takes place by diffusion of the active ingredient into the skin and, via the vessels present therein, into the patient's blood stream.

Transdermal therapeutic systems usually comprise an active ingredient depot, a backing layer that is impermeable to the active ingredient, and a protective film, which is removed before application of the system. At present, two basic types of transdermal therapeutic systems are known, matrix systems and reservoir systems. In so-called matrix systems, the active ingredient is contained in a polymer matrix which is mostly formed of a self-adhesive pressure-sensitive polymer. Delivery of the active ingredient is controlled via the concentration gradient to the skin. In so-called reservoir systems, the active ingredient is contained in a liquid, semi-solid or solid reservoir, delivery of the active ingredient being regulated by means of a membrane.

For application of a transdermal therapeutic system, also referred to as a patch hereinbelow, the protective film of the patch is first removed before the system is attached to the skin. For better gripping, and in order thus to facilitate removal of the protective film, the protective film in some patches projects beyond the edge of the remainder of the patch. Other transdermal therapeutic systems use a two-part protective film, the adjoining edges of which stand up when the patch is bent and can thus be gripped without touching the region of the patch containing the active ingredient. In order to minimise the risk of contaminating the fingers when applying the patch to the skin, it is generally recommended first to remove only one part of the two-part protective film, while at the same time holding the patch by the region that is covered by the other part of the protective film, to apply the exposed portion of the patch to the skin, and then to remove the second part of the protective film. In order to further reduce the risk of contamination, both parts of the protective film are arranged to overlap in some transdermal therapeutic systems.

However, it has been found in practice that it is often difficult, and especially for people with limited motor function, to remove the protective film from a transdermal therapeutic system without touching a region of the patch containing the active ingredient. This is the case especially for relatively small TTS.

It is therefore desirable to provide a transdermal therapeutic system which can be applied more easily.

Embodiments of such a transdermal therapeutic system comprise an active ingredient depot containing at least one active ingredient, an application face which is designed for application to a skin and which is adhesive on at least some parts of the surface, and a protective film which covers the application face and which comprises a first protective film part and a second protective film part, wherein the first protective film part differs in terms of its physical properties from the second protective film part.

The application face is to be understood as being the face of the transdermal therapeutic system that is provided for contact with the skin. The application face can be designed to be adhesive over its entire surface, for example if the active ingredient depot itself is adhesive or is coated over its entire surface with a pressure-sensitive adhesive, or to be adhesive only on some parts of the surface, for example by enclosing the active ingredient depot in an adhesive ring with the aid of, for example, a covering plaster or overtape.

In order to reduce a possible contamination risk, the rear face of the active ingredient depot remote from the application face can be covered with a backing layer, which is preferably impermeable to the active ingredient.

In preferred embodiments of such transdermal therapeutic systems, the different physical properties include different surface tensions of the protective film parts on the sides facing the application face, as a result of which different strengths of adhesion of the protective film parts to the application face is achieved.

In further preferred embodiments of such transdermal therapeutic systems, the different physical properties include different thicknesses of the protective film parts, as a result of which different take-off efficiencies can be achieved in a simple manner. The different physical properties can further also include the stiffnesses of the protective films, which are adjusted, for example, by specific methods such as, for example, stretching or plasticisers in order thereby to achieve different take-off efficiencies.

In further advantageous embodiments, the different physical properties include different surface structures of the protective film at least on the sides facing the application face, as a result of which contact surfaces of different sizes and, associated therewith, adhesive powers that differ from one another are created. In specific configurations of such embodiments, the surface structure of a protective film part is formed by an embossed structure. In other embodiments, the surface structure of a protective film part is formed by the roughness of its surface.

The different physical properties advantageously include in embodiments the formation of the protective film parts from different materials, because both different adhesive properties and different take-off efficiencies can thereby be achieved.

In embodiments, the first protective film part and/or the second protective film part can have a coating on the side facing the application face, the coating(s) being so designed that the protective film parts adhere to the application face with different strengths.

For better handling, the two protective film parts differ in preferred embodiments in the colouration of their surfaces remote from the application face, so that the protective film part that is easier to remove can easily be identified visually.

Figure 3:
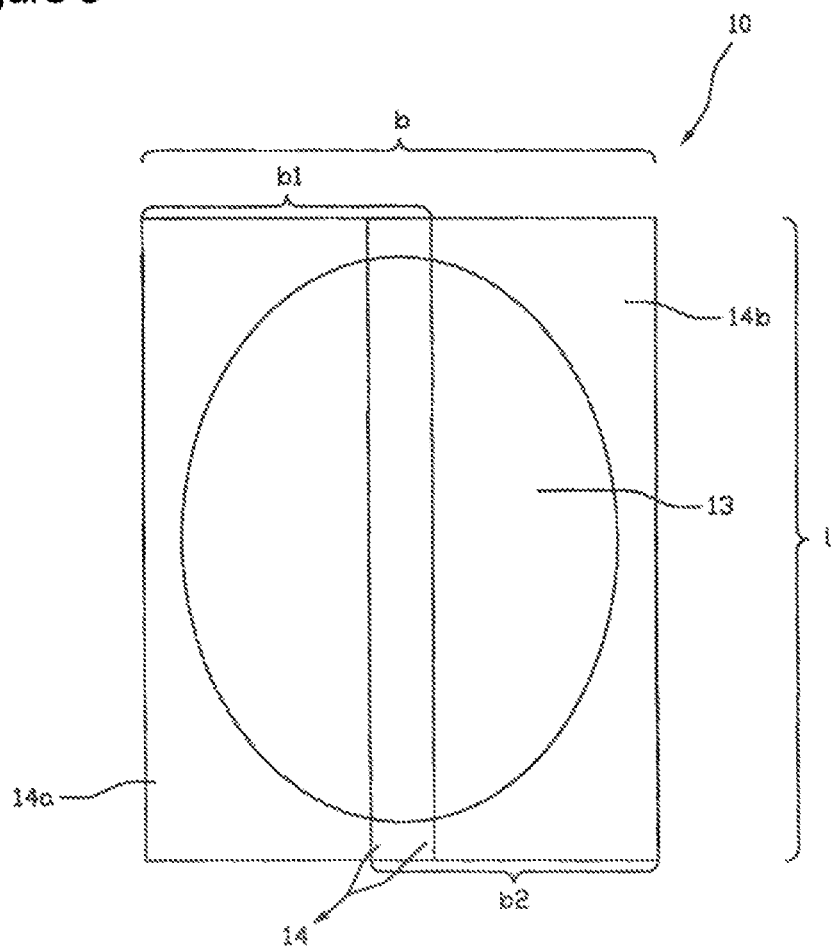
Figure 4:
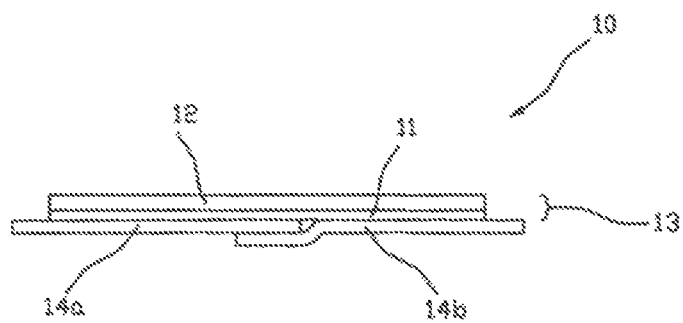
Figure 5:
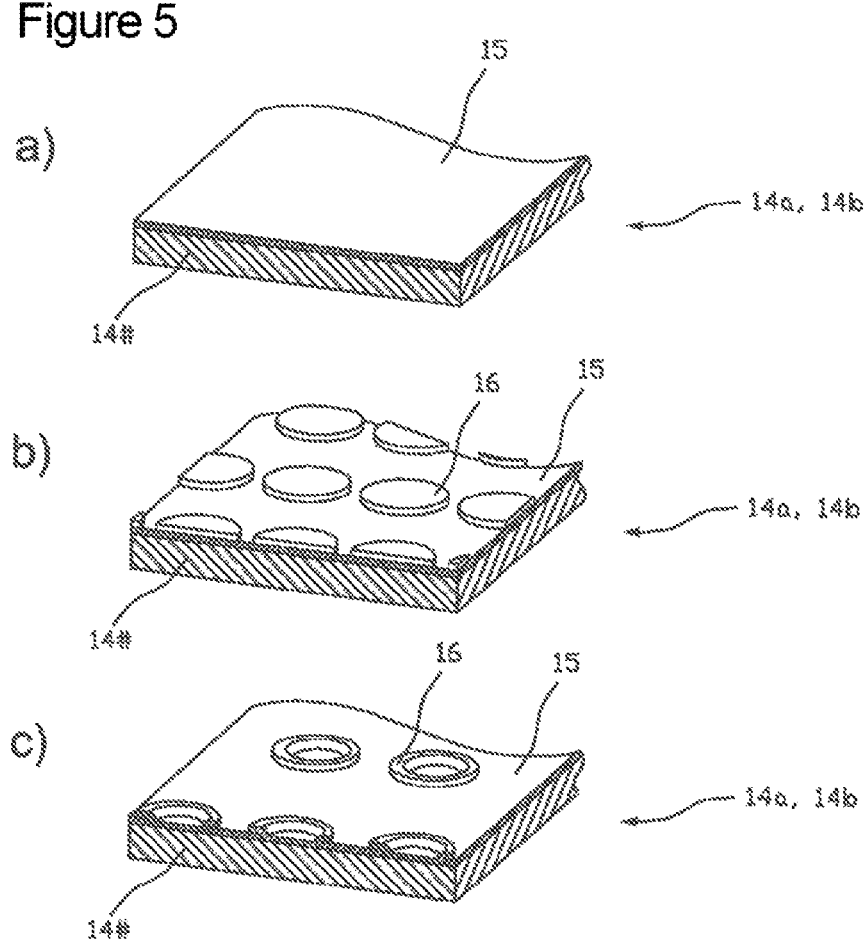
Figure 6:
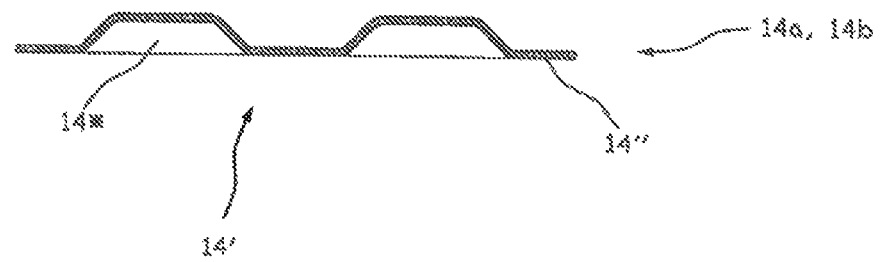

Further features of the invention will become apparent from the following description of embodiments in conjunction with the claims and the accompanying figures. It should be noted that the invention is not limited to the embodiments of the described embodiments but is determined by the scope of the accompanying claims. In particular, in embodiments according to the invention, the features mentioned in connection with the embodiments discussed below can be realised in a number and combination other than that given in the examples. In the following explanation of some embodiments of the invention, reference is made to the accompanying figures, in which FIG. 1 shows, in a schematic representation, a cross-section through a transdermal therapeutic system with improved removability of the protective film, FIG. 2 shows a schematic bottom view of various configurations of a transdermal therapeutic system configured according to FIG. 1, FIG. 3 shows a schematic representation of a bottom view of a transdermal therapeutic system with improved removability of the protective film, in which protective film parts partially overlap, FIG. 4 shows a schematic cross-sectional representation of the transdermal therapeutic system of FIG. 3, FIG. 5 shows schematic perspective representations of various embodiments of coated protective film parts, and FIG. 6 shows a schematic representation of a cross-section through part of a three-dimensionally structured protective film part.

In the figures, the same or similar reference numerals are used for features which are functionally equivalent or similar, irrespective of specific embodiments.

The schematic cross-sectional representation of FIG. 1 shows a transdermal therapeutic system 10 with improved removability of the protective film. FIG. 2 shows in the representations a) to f) schematic bottom views of various embodiments of patches 10 having a structure corresponding to FIG. 1.

Figure 2:
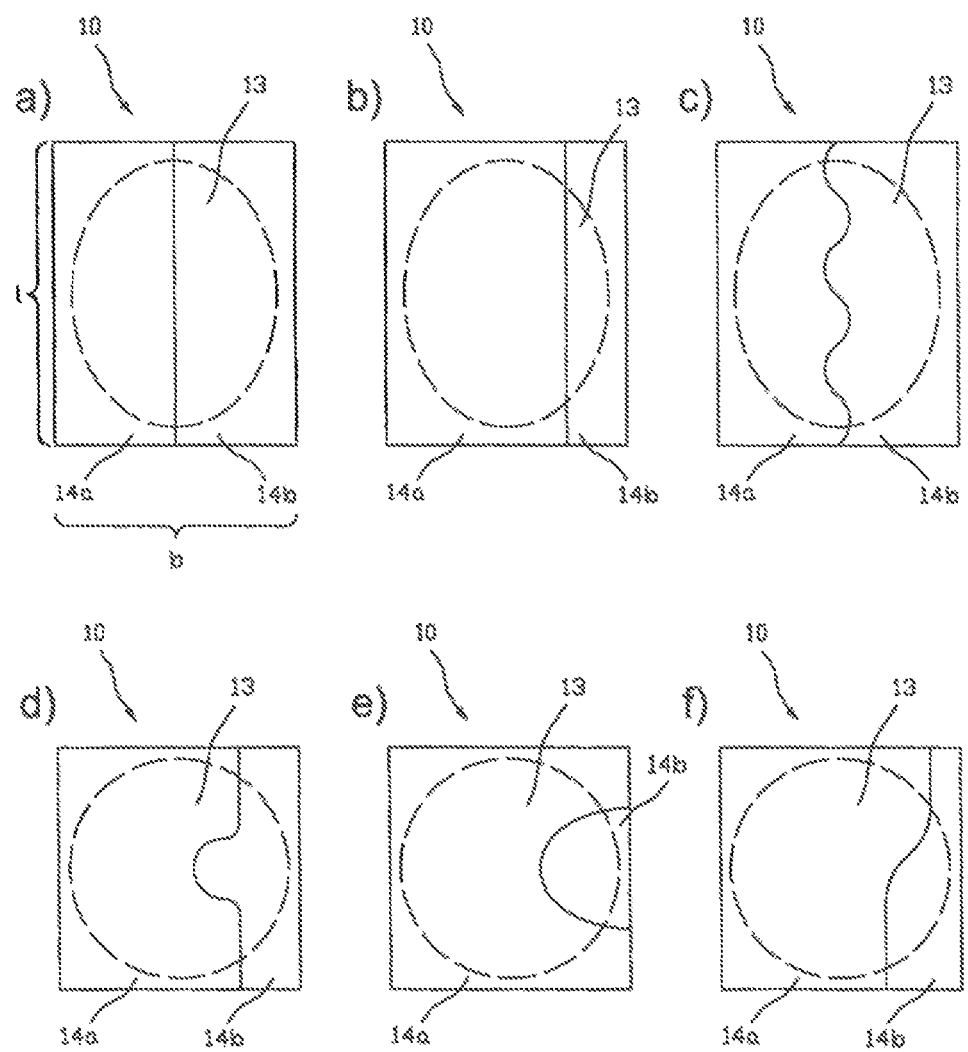

The patches 10 shown in FIGS. 1 and 2 comprise a backing layer 12, which is formed by a film that is impermeable to the active ingredient. The backing layer 12 covers the rear side of the active ingredient depot 11 arranged beneath it. On the side of the active ingredient depot remote from the backing layer 12, the active ingredient depot 11 is covered by a protective film 14 formed by the two protective film parts 14a and 14b. In order to facilitate removal of the protective film parts 14a and 14b from the active ingredient depot 11, the two protective film parts have different physical properties, as will be described in greater detail below.

In the embodiments shown, the two protective film parts 14a and 14b are immediately adjacent to one another at one of their edges, so that they together form a closed surface of width b and length l. The protective film 14 can, of course, also have a form other than a rectangular shape. For application of the patch 10 to the skin of a patient, the two protective film parts 14a and 14b are removed from the active ingredient depot 11, and the skin-side surface, free of the protective film 14, of the laminate 13 formed by the active ingredient depot 11 and the backing layer 12 is applied to the skin.

In the patches 10 shown in FIGS. 1 and 2, the lateral dimensions of the laminates 13, that is to say their dimensions transverse to the layer sequence, are always smaller than the dimensions of the protective film 14 covering the laminate 13 in question, the laminates 13 being arranged wholly within the edges of the protective film. The protective films 14 accordingly have an edge region that is not covered by the laminate 13, at which they can be gripped for removal without the risk of touching an active-ingredient-containing part of the laminate 13. For application, the more easily removable protective film part of such a patch is removed first, and the exposed skin-side region of the laminate 13 is then applied to the application site, the system being held in the region of the other protective film part. The second protective film part can then be gripped in the free edge region and pulled off either directly or by bending the patch, as a result of which the whole of the surface of the laminate comes to rest on the skin.

A further embodiment of a transdermal therapeutic system 10 with improved removability of the protective film 14 is shown schematically in FIGS. 3 and 4. In contrast to configurations according to FIGS. 1 and 2, in this embodiment, the two protective film parts overlap in part. Such embodiments are preferred in systems 10 in which the active ingredient depot 11 has a tendency to cold flow and could escape from between protective film parts arranged edge to edge.

The shape and size of laminates 13 and protective films 14 of transdermal therapeutic systems 10 are not limited to the embodiments shown in FIGS. 1 to 4. In fact, on condition that the protective film 14 covers the skin-side surface of the laminate 13 completely, they can be chosen freely according to the intended use of a particular transdermal therapeutic system so that, apart from the round, oval and rectangular forms shown, there can be used in particular also annular forms, star-shaped forms or forms with wavy edges. Furthermore, the laminate 13 and the protective film 14 can be of the same size, so that the protective film does not project beyond the edge or edges of the laminate.

The transdermal therapeutic system 10 can be in the form of both a matrix system and a reservoir system. The active ingredient depot formed by a matrix or a reservoir is covered on one side by a backing layer 12 that is impermeable to the active ingredient, or is enclosed by such a layer also at the side faces. The application face, which is remote from that side, of the active ingredient depot is used to establish contact with the skin of patient. The application face is adhesive, which is to be understood as meaning that the active ingredient depot itself is adhesive, is provided on the skin side with a self-adhesive layer or is enclosed by an adhesive edge.

When in the form of a matrix system, the active ingredient depot 11 preferably comprises a matrix which contains the active ingredient and is based on a pressure-sensitive adhesive. All suitable materials conventionally used for transdermal therapeutic systems, such as homo- and co-polymers of (meth)acrylates, polyvinyl ethers, polyisobutylenes, polyisoprene rubbers, styrene-butadiene copolymers or styrene-butadiene-styrene copolymers and silicones, are suitable for forming the matrix. Among the (meth)acrylate copolymers, mention may be made, for example, of the copolymers of alkyl acrylates and/or alkyl methacrylates and further unsaturated monomers, such as acrylic acid, methacrylic acid, acrylamide, dimethylacrylamide, dimethylaminoethylacrylamide, acrylonitrile and/or vinyl acetate. In principle, it is naturally also possible to provide a self-adhesive matrix system with a further adhesive layer on the skin side, for example in order further to improve the adhesion to the skin. Alternatively or in addition, a covering layer conventionally referred to as an overtape, which covers the matrix and is provided with a pressure-sensitive adhesive on the skin side, can be used.

When the transdermal therapeutic system 10 is in the form of a reservoir system, the active ingredient is usually contained in a liquid or a gel, the active ingredient reservoir having on the skin side a membrane by which the delivery of the active ingredient to the skin is controlled. In reservoir systems, the skin-side surface of the laminate 13 is preferably coated with a pressure-sensitive adhesive, in order to allow the protective film to adhere thereto and the patch to be fixed to the skin. Alternatively or in addition, it is possible here too to use a covering layer which covers the reservoir and is provided with a pressure-sensitive adhesive on the skin side, which covering layer encloses the reservoir within an adhesive edge.

In this specification, pressure-sensitive adhesives, also called contact adhesives, are understood as being adhesives which, on contact with a material surface, adhere thereto. The interfacial properties of such an adhesive compound are determined by the interfacial tensions, also referred to as surface tensions, at the interface between the surface of the material and the surface of the adhesive. The formation of an adhesive bond requires the surface of the material to be wetted by the adhesive, for which purpose the interfacial tension of the adhesive must not be higher than that of the surface of the material. Only then is the force of attraction of the adhesive to the surface of the material higher than to itself, so that it can flow on the surface of the material.

The removability of a protective film applied to a contact adhesive is determined by the separating force required to remove the film and the effectiveness with which the separating force can be applied. While the separating force required for removal increases with the adhesive power of the adhesive compound and is thus determined substantially by the wetting of the protective film by the adhesive, the effectiveness of the application of the separating force is determined by physical properties of the protective film, which act on the conversion of a tensile force applied on removal of the protective film into a separating force and accordingly are different from surface tensions. The flexibility and resilience of the protective film material are primarily of importance for the conversion of a tensile force into a separating force.

For removal, a protective film part is generally gripped at one of its edge regions, and the gripped region is then pulled over the region of the laminate covered by the gripped protective film part. The resulting bending radius of the protective film part is greater, the stiffer the protective film part, or is smaller, the more flexible the protective film part. Flexibility is here understood as being the property of a material to bend as a result of a force acting perpendicularly to one of its surfaces. The smaller the bending radius on removal of the protective film part, the greater the force component oriented perpendicularly to the interface between the adhesive and the protective film at the transition from the region of the protective film part that has already been removed to the region that is still adhering to the adhesive. Because this component is critical for releasing the bonds at the interface, more flexible protective film parts can be removed from a pressure-sensitive adhesive more easily than can stiffer protective film parts. Embodiments of a transdermal therapeutic system with a protective film formed by protective film parts of different removability therefore have at least two protective film parts of different stiffness or, conversely, of different flexibility.

A possible way of forming protective film parts of different flexibility or stiffness is to produce the two protective film parts using different materials. Suitable protective film materials are, for example, polyethylenes, such as HDPE, polypropylenes, polyesters, polysiloxanes, polyethylene terephthalates, polyvinyl chlorides or polyurethanes, optionally in the form of laminates. Suitable protective films are obtainable, for example, from 3M under the trade mark Scotchpak® (such as Scotchpak® 1020, 1022, 9736, 9742, 9744, 9755), from Siliconature, for example, under the name Silthene or Silphan, from Mitsubishi under the trade mark Hostaphan® (e.g. GN, RD) or from Loparex Inc. under name FL2000.

Apart from the choice of material, the flexibility and stiffness of a protective film part can also be influenced by way of its thickness, so that in embodiments the film thickness of one of the protective film parts 14a differs from that of another of the protective film parts 14b. Of course, the protective film parts can differ both in terms of the film material and in terms of the film thickness. In order not to impair the removability of the protective film parts, the material and the thickness should be so chosen that the protective film parts do not have significant resilience, that is to say they do not stretch noticeably under the forces required for their removal. The thickness can be suitably chosen on the basis of the properties of the material, it being possible to specify as the range, for example, the range from 10 to 70 µm for a first protective film part and the range from 75 to 150 µm for a second protective film part.

The second factor that is important for the removability of a protective film part 14a or 14b is its adhesive power to the adhesive surface of a transdermal therapeutic system 10. This is influenced by the surface tension of the surface of the protective film part that is in contact with the adhesive surface. In embodiments of transdermal therapeutic systems 10, the protective film parts 14a and 14b therefore differ in terms of the surface tension at their contact surface provided for application to a laminate 13. The surface tensions of the contact surfaces can be reduced by silicone, fluoropolymer or fluorosilicone coating, the choice of coating 15 being matched to the adhesive used on the application face or skin side of the laminate. The perspective sectional representation of FIG. 5a shows a protective film part 14a or 14b which is formed by a film material 14# coated over the entire contact surface. The protective film part having lower surface tension at the contact surface has lower adhesion to the laminate 13 and therefore requires a smaller separating force for its removal.

The coating with the lower surface tension does not have to cover the entire laminate-side surface of a particular protective film part. In order to achieve a lower power of adhesion of the protective film part to a laminate 13, it is sufficient to coat the contact surface of the protective film part, that is to say the surface region which is used to cover the contact adhesive. In the case of larger patches, the coating with lower surface tension can also be limited to a partial region of the contact surface, said partial region being formed by the region that is to be detached first on removal of the protective film part.

In further configurations, at least one of the two protective film parts 14a or 14b has two coatings with different surface tensions, one of the coatings covering part of the surface of the laminate-side surface of each protective film part in the form of a pattern. This patterned coating 16 can, as is shown schematically in FIG. 5b, be arranged on a coating 15 applied beforehand to the entire surface or, as is shown in FIG. 5c, can cover surface regions of the protective film base material that are not covered by a first coating 15 which is likewise patterned. In the last-mentioned case, the patterns of the two coatings 15 and 16 can be configured so that they do not overlap, as is shown, but rather are complementary.

In further configurations of the above-described embodiments, the wettability of the laminate-side surface of one of the protective film parts is reduced by bringing the surface into contact with a pressure-sensitive adhesive before it is applied to the laminate 13 and then detaching it therefrom again. On removal, residues of adhesive remain on the protective film part and determine the local surface tension of the protective film part at those points. When using contact adhesives whose surface tension is lower than that of the laminate-side surface of the protective film part, the adhesive power of the protective film part to the skin side of the laminate 13 can thus be reduced. This method can also be used in the case of coated protective film parts 14a and 14b, whereby the residues of adhesive in particular fill pores in the coating.

Apart from the surface tension, the adhesion of protective film parts 14a and 14b to a laminate 13 is also determined by the ratio of the contact surface to the covering surface on the contact side of a protective film part. The contact surface is here understood as being the surface of a protective film part that is wetted by the contact adhesive, and the covering surface is understood as being the surface of the adhesive that is covered by the protective film part. A reduction in the adhesive power of a protective film part to a laminate 13 is therefore effected in further embodiments with the aid of a three-dimensional structuring of one or both protective film parts 14a and/or 14b. An example of a correspondingly configured protective film 14 is shown schematically in the cross-sectional representation of FIG. 6. The protective film parts 14a and 14b have depressions 14*, which are formed, for example, by means of embossing. The depressions are generally not filled by the contact adhesive of a laminate 13 covered by the protective film and the bottom of the depressions is accordingly not wetted by the adhesive. If both protective film parts 14a and 14b have a three-dimensional structuring, then the contact surface 14" provided for contact with the pressure-sensitive adhesive is smaller in one of the two protective film parts than in the other.

In the case of a contact adhesive that has a tendency to cold flow, it is possible that the depressions of a protective film part will be filled and the structured surface will accordingly result in a larger wetting surface. The person skilled in the art can adjust the ratio of the contact surface to the covering surface in the desired manner according to the system.

This can be achieved, for example, in that the lateral dimensions of the depressions of one of the two protective film parts are larger than those of the other.

A smaller contact surface 14" compared with the covering surface can also be achieved by way of the roughness of the contact face 14' of a protective film part 14a or 14b. In the case of sufficiently rough surfaces, contact between an adhesive that does not have a tendency to cold flow and the film material can be achieved only at the "peaks" of the film surface. The valleys are in this case not wetted by the adhesive. In order to form a protective film 14 with improved removability, it is therefore possible to use a film material in which the two surfaces have different topographies, for example a smooth surface and a rough surface, the two protective film parts 14a and 14b each being applied to the pressure-sensitive adhesive with a different side. Examples of such film materials which may be mentioned are the PET films Hostaphan® RD and RD 26HC from Mitsubishi Polyester Film. In the case of adhesives that have a tendency to cold flow, greater roughness of the contact side of a protective film part can lead to a larger wetting surface and accordingly to a higher adhesive power.

The above also applies analogously to the use of protective films 14 having more than two protective film parts. Furthermore, the described measures, as has already been mentioned above, can also be limited to a partial region of the contact surface, as long as that partial region forms the region of the protective film part that is detached first on removal from a laminate 13.

Known test methods can be used to determine the removability of the protective film parts. For example, an adhesive force measurement according to a corresponding DIN specification such as DIN EN 1939 can be carried out. The separating force can be determined, for example, using a FINAT (Féderation international des fabricants et transformateurs d'adhésifs et thermocollants sur papiers et autres supports) test such as FTM 3 and 4. Because the improvement in the removability of the protective film is achieved primarily by the relative differences in the removability of the protective film parts and less by the separating force that is to be applied absolutely, it is also possible to use a different conventional method for determining adhesive power or separating force, provided that the measurement is carried out by the same method for both protective film parts.

In embodiments, the above-described different measures for achieving a mutually different adhesive power or separating force of the protective film parts can, of course, be combined with one another and with the above-described measures for achieving a different efficiency of the conversion of a tensile force into a separating force.

In order to facilitate the identification of the more easily removable protective film part, that protective film part is preferably distinguished from the other protective film part or parts in terms of colour, for example by a particular colouration of its visible surface, which is generally remote from the application face of the laminate 13. A coloured or printed film material can be used to achieve a different colouration. Moreover, the protective film part that is to be removed first can also be made recognisable by an appropriate marking or a gripping tab.

Two examples are described below, in which the protective film 14 is formed by two protective film parts 14a and 14b having different physical properties.

In order to investigate the separating properties of the different protective film parts, transdermal therapeutic systems comprising a matrix of an adhesive acrylate-vinyl acetate copolymer were prepared. Each TTS was provided with a combination of in each case two different protective film parts 14a and 14b which are coated on the surface. A first protective film part (14a) was first applied with the coated surface to part of the adhesive surface of the matrix. The second protective film part (14b) was then applied to the uncovered, free part of the adhesive surface of the matrix so that it overlapped with the first protective film part (14a). Here too, the coated side of the second protective film part (14b) faced the adhesive surface of the matrix.

There was used as the first protective film part a silicone-coated polyester film having a thickness of 50 µm, which is commercially available from Loparex Inc. under the name FL2000/50 µm, or a fluoropolymer-coated polyester film having a thickness of 74 µm, which is commercially available from 3M under the name Scotchpak™ 9755. There was used as the second protective film part a silicone-coated polyester film having a thickness of 100 µm, which is marketed by Loparex Inc. under the name FL2000/100 µm, or a fluoropolymer-coated polyester film having a thickness of 74 µm, which is commercially available from 3M under the name Scotchpak™1020.

The TTS were stored for 2 days at room temperature. After this equilibration time, the take-off force of the individual protective film parts (14a, 14b) was determined by means of a tensile tester (EZ test, Shimadzu, Germany), the take-off force being the force necessary to detach the protective film part from the adhesive matrix. The specific take-off angle is 90° in the present case, and the take-off speed is 300±30 mm/minute. The test specimen was fixed to the smooth surface of the specimen block in such a manner that the protective film parts faced upwards. The measured values were evaluated standardised to a sample width of 25 mm and represent the mean value of 3 or 2 (Scotchpak™ 1020) measurements. The results are summarised in the table below.

TABLE

| | Take-off force [N/25 mm] |
|---|---|
| Protective film part 1 | |
| FL2000/50 μm | 0.063 |
| Scotchpak ™ 9755 | 0.065 |
| Protective film part 2 | |
| FL2000/100 μm | 0.082 |
| Scotchpak ™ 1020 | 0.306 |

It is clear from the table that different take-off forces are obtained with the same coating but a different thickness of the protective film material. The same is also true of protective films of the same thickness but with different surface coatings.

The described invention permits a transdermal therapeutic system with improved removability of the protective film, which allows even persons with limited motor capabilities to attach the patch to a skin simply and without the risk of undesirable contamination of body regions or objects.

The invention claimed is:

1. A transdermal therapeutic system comprising:
an active ingredient depot containing at least one active ingredient;
a backing layer covering a first surface of the active ingredient depot;
an application face on a second surface of the active ingredient depot, opposite the first surface, the application face having a skin-contacting surface that is designed for application to a skin, the application face being adhesive on at least some parts of the skin-contacting surface; and
a protective film that covers the application face and comprises a first protective film part having a first edge and contacting and covering a first portion of the application face, and a non-overlapping second protective film part having an edge immediately adjacent to the first edge and contacting and covering a second portion of the application face,
wherein the second portion is different from the first portion, and the first protective film part differs, in terms of its physical properties, from the second protective film part such that the first protective film part has a different strength of adhesion to the application face compared with the strength of adhesion of the second protective film part to the application face, the first protective film part has a different removability from the application face compared with the removability of the second protective film part from the application face, and the first protective film part has a different thickness compared with the second protective film part.

2. The transdermal therapeutic system according to claim 1, wherein the different physical properties include different surface tensions of the first and second protective film parts on respective sides of the first and second protective film parts facing the application face.

3. The transdermal therapeutic system according to claim 1, wherein the thickness of the first protective film part is from 10 μm to 70 μm and the thickness of the second protective film part is from 75 μm to 150 μm.

4. The transdermal therapeutic system according to claim 1, wherein the different physical properties include different stiffnesses of the first and second protective film parts such that the first protective film part has a different flexibility compared with the flexibility of the second protective film part.

5. The transdermal therapeutic system according to claim 1, wherein the different physical properties include different surface structures of the first and second protective film parts on at least sides facing the application face.

6. The transdermal therapeutic system according to claim 1, wherein the first protective film part, the second protective film part, or both, have a coating on a side facing the application face.

7. The transdermal therapeutic system according to claim 1, wherein the first and second protective film parts differ from one another in the coloration thereof.

8. The transdermal therapeutic system according to claim 1, wherein the first protective film part comprises a first material and the second protective film part comprises a second material that differs from the first material.

9. A transdermal therapeutic system comprising:
an active ingredient depot containing at least one active ingredient;
an application face on a surface of the active ingredient depot, the application face having a surface that is designed for application to the skin, the application face being adhesive on at least some parts of the surface; and
a protective film that covers the application face and comprises a first protective film part covering a first portion of the application face, and a second protective film part covering a second portion of the application face,
wherein the second portion is different than the first portion, and the first protective film part differs, in terms of its physical properties, from the second protective film part such that the first protective film part has a different strength of adhesion to the application face compared with the strength of adhesion of the second protective film part to the application face, the surface structure of one of the first and second protective film parts is formed by embossed depressions that provide a three-dimensional structuring that differs from three-dimensional structuring of the other of the first and second protective film parts, the first protective film part has a different removability from the application face compared with the removability of the second protective film part from the application face, and the first protective film part has a different thickness compared with the second protective film part.

10. The transdermal therapeutic system according to claim 9, wherein the application face comprises a pressure-sensitive adhesive, each of the first and second protective film parts comprises three-dimensional structuring, the first protective film part contacts the pressure-sensitive adhesive at a contact surface having a first surface area, and the second protective film part contact the pressure-sensitive adhesive at a contact surface having a second surface area that is smaller than the first surface area.

11. The transdermal therapeutic system according to claim 9, wherein the first protective film part has a different flexibility compared with the flexibility of the second protective film part.

12. A transdermal therapeutic system comprising:
an active ingredient depot having a skin-contacting surface and an opposite, back surface;
a backing layer in contact with and covering the back surface; and a protective film in contact with and covering the skin-contacting surface, wherein the protective film comprises an exposed edge region that extends past and does not contact the active ingredient depot, the protective film comprises a first protective film part and a second protective film part that overlaps the first protective film part, and the first protective film part has physical properties that differ from physical properties of the second protective film part such that the first protective film part has a different strength of adhesion to the application face compared with the strength of adhesion of the second protective film part to the application face, and the first protective film part has a different removability from the application face compared with the removability of the second protective film part from the application face, and the first protective film part has a different thickness compared with the second protective film part.

13. The transdermal therapeutic system according to claim 12, wherein the active ingredient depot comprises an active ingredient and the backing layer is impermeable to the active ingredient.

14. The transdermal therapeutic system according to claim 12, wherein at least one of the first protective film part and the second protective film part comprises embossed depressions that provide the respective protective film part with a three-dimensional structuring.

15. The transdermal therapeutic system according to claim 12, wherein the first protective film part exhibits a stiffness and the second protective film part exhibits a different stiffness compared to that of the first protective film part.

16. The transdermal therapeutic system according to claim 12, wherein the first protective film part and the second protective film part have respective contact surfaces that contact the active ingredient depot, and the contact surface of the first protective film part, the second protective film part, or both, has or have a coating at the respective contact surface.

17. The transdermal therapeutic system according to claim 16, wherein the contact surface of the first protective film part exhibits a first surface tension, and the contact surface of the second protective film part exhibits a second surface tension that differs from the first surface tension.

18. The transdermal therapeutic system according to claim 12, wherein the first protective film part comprises a film that is coated with a first coating and the second protective film part comprises a film that is coated with a second coating that comprises a different material than the first coating.

19. The transdermal therapeutic system according to claim 12, wherein the first protective film part comprises a polyester film of a first thickness and coated with a first coating, and the second protective film part comprises a polyester film of the same first thickness but coated with a different coating than the first coating.

20. The transdermal therapeutic system according to claim 12, wherein the first protective film part comprises a polyester film that is coated with a first fluoropolymer, and the second protective film part comprises a polyester film that is coated with a different fluoropolymer.

21. The transdermal therapeutic system according to claim 12, wherein the first protective film part comprises a first material and the second protective film part comprises a second material that differs from the first material.

22. The transdermal therapeutic system according to claim 12, wherein the thickness of the first protective film part is from 10 μm to 70 μm and the thickness of the second protective film part is from 75 μm to 150 μm.

* * * * *